United States Patent

Wool

[11] Patent Number: 4,566,305
[45] Date of Patent: Jan. 28, 1986

[54] SWEEP-ARM BENDER FOR FORMING ORTHODONTIC ARCHES

[76] Inventor: Arthur L. Wool, 1402 Penn Ave., Wyomissing, Pa. 19610

[21] Appl. No.: 609,288

[22] Filed: May 11, 1984

[51] Int. Cl.[4] ............................................. B21D 11/04
[52] U.S. Cl. ......................................... 72/321; 72/387; 72/384; 72/309; 72/323; 140/102.5
[58] Field of Search ................. 72/387, 384, 381, 308, 72/309, 310, 477, 217, 218, 219, 321, 323, 461, 306; 140/102.5

[56] References Cited

U.S. PATENT DOCUMENTS

| | | | |
|---|---|---|---|
| 528,036 | 10/1894 | Seaton | 72/219 |
| 533,965 | 2/1895 | Richard | 72/219 |
| 706,010 | 8/1902 | Benson | 72/477 |
| 1,054,675 | 3/1913 | Coffman | 72/219 |
| 2,141,010 | 12/1938 | Minister | 153/46 |
| 3,229,727 | 1/1966 | Kenlon | 140/102.5 |
| 3,538,737 | 11/1970 | Del Monica | 72/310 |
| 3,901,064 | 8/1975 | Jacobson | 72/388 |
| 3,979,938 | 9/1976 | Thompson | 72/217 |
| 4,167,865 | 9/1979 | Powell | 72/217 |

OTHER PUBLICATIONS

Duo-Mite Bulletin of Mark Eyelet & Stamping, Inc., Copyright 1980.

Primary Examiner—Daniel C. Crane
Assistant Examiner—David B. Jones
Attorney, Agent, or Firm—Howson and Howson

[57] ABSTRACT

A device for forming orthodontic arches from straight wire blanks comprises a die having a cylindrical surface with multiple wire-receiving grooves situated in planes perpendicular to the die axis. A clamp temporarily applies a clamping force to the wire blank, thereby firmly holding a portion of the wire blank in the groove of the die. The bender has two sweep arms, each pivoted on the die axis. A slide is provided on each of the sweep arms, and is constrained for movement toward and away from the die axis. Each slide carries a circular cylindrical roller mounted in bearings on the slide, for rotation about a roller axis parallel to the die axis. An adjustable toggle mechanism on each arm temporarily locks its roller in a position such that the outer roller surface presses the wire blank into one of the wire-receiving grooves before the arm begins to sweep about the die axis, and throughout the sweeping movement of the arm. Each of the arms is pivotable from a position in which its roller is located adjacent to the clamp to a position beyond the position in which its roller is directly opposite to the clamp. A pivoted positioning block insures symmetry in the arch by engaging one end of the blank and thereby insuring that the exact center of the blank is tangent to the die. The block pivots out of the way to provide clearance for arm movement. The die grooves can be configured to pretorque the arches automatically in the forming operation.

10 Claims, 16 Drawing Figures

SWEEP-ARM BENDER FOR FORMING ORTHODONTIC ARCHES

BRIEF SUMMARY OF THE INVENTION

This invention relates generally to wire bending, and more specifically to a sweep-arm bender for forming orthodontic arches from straight wire blanks.

Sweep-arm benders have been used in the past for the formation of elliptical or modified cylindrical shapes for bracelets, jewelry and the like, and, more generally, for bending metal into various shapes. Sweep-arm benders have numerous advantages over other forms of bending devices, including simplicity, reliability, ruggedness, ease of use, and versatility in the sense that they can be easily adapted for bending different metal parts into a wide variety of shapes.

A typical sweep-arm bender, used in the manufacture of jewelry items such as bracelets and the like, is described in U.S. Pat. No. 4,167,865, dated Sept. 18, 1979. The patent describes a hand-operated bender comprising a frame, a die, a die-supporting pin extending upwardly from the frame, a clamping device for holding a piece of metal to be formed against the die, and a sweep arm movable about a pivot located underneath the die on the die pin axis. The sweep arm carries a spring-loaded slide with a series of holes any one of which can be selected to receive a work-engaging pin. Bending is initiated with the sweep arm on one side of the frame, and with the work-engaging pin in contact with the work at a location at which the work is spaced from the die. The arm is moved about the die to form a first bend in the work. The pin is then removed, and the arm is moved to the opposite side of the frame, where a second bending operation is carried out to complete the formation of the jewelry item. The bending apparatus as disclosed in U.S. Pat. No. 4,167,865 is not suitable for use in the formation of orthodontic wires. It is an object of this invention to provide improvements on the sweep-arm bender of U.S. Pat. No. 4,167,865 which make the bender suitable for forming orthodontic arches from straight wire blanks. This object is achieved in accordance with the invention by the adoption of a number of features which, alone, and in combination, eliminate problems with the prior bending apparatus which render it unsuitable for orthodontic work.

One of the important features of the invention resides in the provision of a slide on the sweep arm which carries a roller, which is designed so that the roller can come into contact with the wire blank at a location adjacent to the point at which the blank is clamped to the die, and which allows the roller to press the wire blank against the die at that location before sweeping movement of the arm begins. Another important feature of the invention is the elimination of springs on the slide, and the substitution of a toggle mechanism, with a device for continuous adjustment of pressure applied by the slide and its roller to the wire blank.

In accordance with the invention, two arms are preferably provided, pivoted on the same axis. The use of two arms makes it unnecessary to remove the slides and rollers in a manner analogous to the removal of the work-engaging pin in U.S. Pat. No. 4,167,865 after finishing the first part of the bending operation and before beginning the second part.

In the bending apparatus of U.S. Pat. No. 4,167,865, a J-shaped positioning device is clamped in the frame. The end of the short leg of the "J" engages the end of the work to locate it in the proper position with respect to the die so that the forming operations are repeatable. Positioning is also necessary in the formation of orthodontic arches. However, a J-shaped positioner would interfere with the roller-carrying slide structure on the sweep arms. Another important feature of the invention, therefore, is the provision of a pivoted positioning block which can be moved to a first position for engagement by the end of a wire blank clamped against the die extending in tangent relationship to the die, and to a second position in which it provides clearance for sweep arm movement.

The die is provided with one or more wire-receiving grooves. These grooves can be cut to conform to rectangular arch wire blanks, and to hold the arch wire blanks at a desired torque angle so that the bending apparatus can automatically pretorque the arches in the course of the bending operation.

It is a further object of the invention to provide a simple and reliable device for forming orthodontic arches, which is sufficiently inexpensive and easy to use that it can be afforded and used on a routine basis by an orthodontist in his office. It is also an object of the invention to provide a device for forming orthodontic arches which can be operated rapidly, which produces high-quality arches, which can be used with wires of any desired cross-sectional size or shape by the simple selection of a suitable die, and which can be used to form pretorqued orthodontic arches.

Various other objects and advantages of the invention will be apparent from the following detailed description when read in conjunction with the drawings.

DETAILED DESCRIPTION

Figure 1:
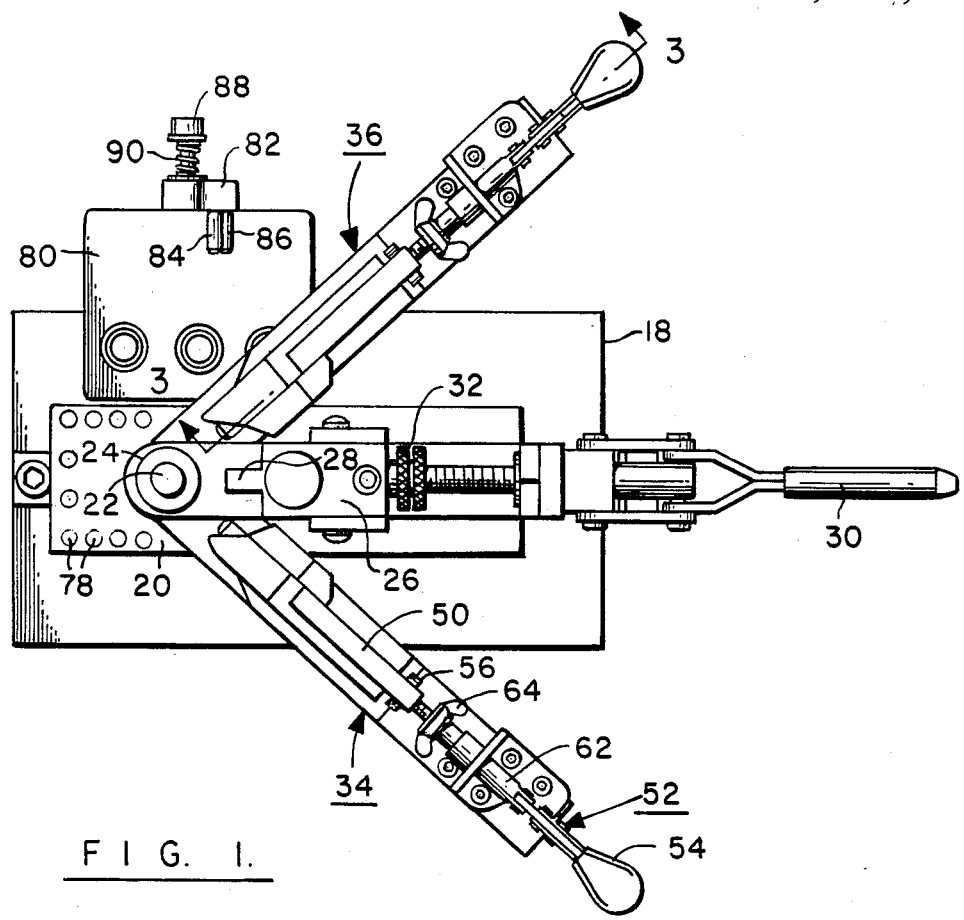
FIG. 1 is a top plan view of a sweep-arm bender in accordance with the invention.
Figure 2:
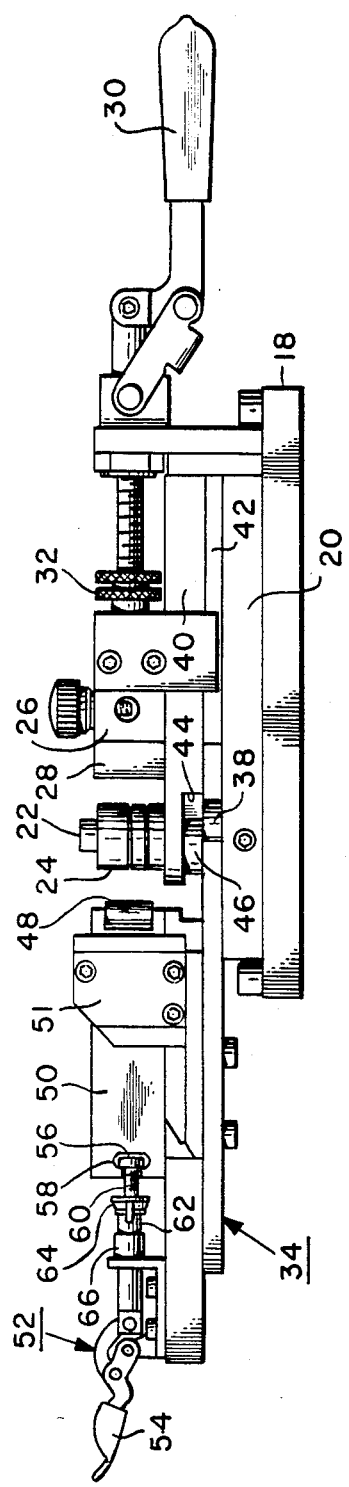
FIG. 2 is a side elevation of the bender with one of the arms extended, and with the other arm omitted for clarity.

As shown in FIGS. 1 and 2, the wire bending device of the invention comprises a base 18, a block 20 fixed to the base, and a pin 22 fixed to, and extending upwardly from, block 20. A removable wire-forming die 24, which is preferably a circular cylinder having at least one groove in its outer cylindrical surface, fits over pin 22, and is secured to pin 22 by a set screw (not shown in FIGS. 1 and 2).

A movable clamping jaw 26, having a wire-engaging face part 28, is movable toward and away from the die by a toggle mechanism operated by handle 30. Adjusting means are provided at 32 for accommodating different sizes of wire. The clamping apparatus is conventional, and reference should be made to U.S. Pat. No. 4,167,865 for details. The disclosure of U.S. Pat. No. 4,167,865 is here incorporated by reference. Briefly, when a wire blank to be foremd into an orthodontic arch is placed in one of the grooves in die 24, it is clamped in place by upward pivoting movement of handle 30, which causes jaw 26 and its wire-engaging face part 28 to move toward the die. The toggle mechanism, if properly adjusted, enables the apparatus to maintain a tight clamping force against the wire until the handle is moved downwardly toward its original position.

As shown in FIG. 1, the device also comprises two sweep arms 34 and 36. In FIG. 2, arm 36 is omitted for clarity, and arm 34 is shown rotated to a position opposite the wire clamping means.

Arm arm 34 is pivoted, at its end 38, on pin 22. Plate 40, which supports die 24, is separated from block 20 by a separator 42. Plate 40 is cut away at 44 to provide space for end 46 of the other sweep arm 36. End 46 is also pivoted on pin 22. Thus, both sweep arms are rotatable about the same axis, which is the axis of the die and of pin 22. Arm 34 carries roller 48, which is a cylindrical hardened steel roller, the cylindrical outer surface of which is adapted to apply pressure to wires held in the grooves of the die in the arch forming operation. Roller 48 is supported in bearings on a slide 50 carried on arm 34 in such a way that its axis always remains parallel to the axis of the die. Slide 50 is constrained by guide 51 for movement toward and away from the die. Movement is effected by a toggle mechanism 52, which is similar to the toggle mechanism of the clamp. The toggle mechanism has an operating handle 54. A head 56 on a threaded rod 60 is situated in a T-shaped slot 58 in the end of slide 50 opposite roller 48. Head 56 can be rotated between the thumb and forefinger for adjustment of the relationship between the slide and the toggle mechanism. Rod 60 is threaded into shaft 62, and locked with respect to shaft 62 by a wing nut 64. Shaft 62 extends through sleeve 66, which is fixed to arm 34 by a bracket. The mechanism just described allows for continuous adjustment of pressure exerted by the roller against the wire. Ordinarily, the extent of pressure required for the forming operation can be determined by feeling the force required to move the toggle mechanism through its dead center position. Because the toggle mechanisms on both arms are identical, it is easy to insure that identical pressures are applied by the rollers on both arms.

Figure 3:
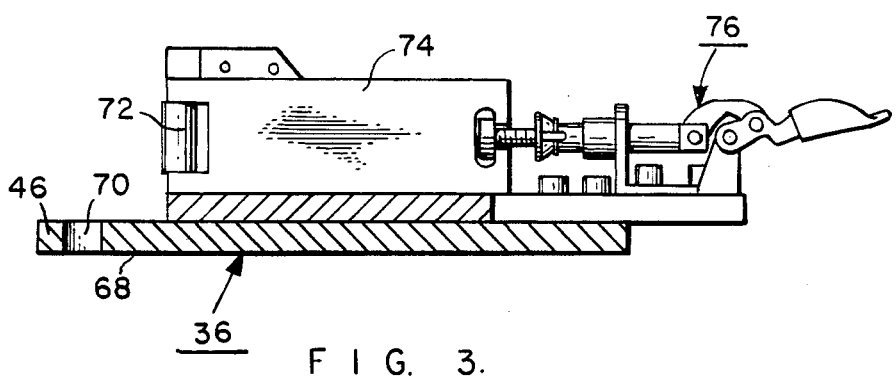
FIG. 3 is a fragmentary sectional view showing one of the sweep arms of the bender.

As shown in FIG. 3, arm 36 comprises a plate 68. A hole 70 in end part 46 of the plate fits over pin 22 (FIG. 2). Roller 72 is held in slide 74, which is operated by toggle mechanism 76. The guide for constraining the slide for movement toward and away from the die is similar to guide 51 in FIG. 2. The rear part of the guide is omitted in FIG. 3 so that the entire slide can be seen.

In the formation of an orthodontic arch wire, symmetry of the wire is of utmost importance. Consequently, it is necessary to assure that the clamping mechanism clamps the wire blank to the die exactly at the center point of the blank. This is accomplished by a pivoted positioning block, the face of which is spaced from the point at which the arch wire blank touches the die by a distance equal to exactly one-half the length of the arch wire blank. A typical arch wire blank is a straight length of wire seven inches long, and the spacing between the positioning block and the point of tangency is therefore exactly three and one-half inches. A plate 80 is fixed to base 18, as shown in FIG. 1. The positioning block 82 has fixed to it two stop pins 84 and 86 which engage plate 80 respectively in the two alternative positions of block 82. Block 82 is pivoted on a pin 88 which is fixed to plate 80. A spring 90 is in compression between a head of pin 88 and block 82.

Figure 4:
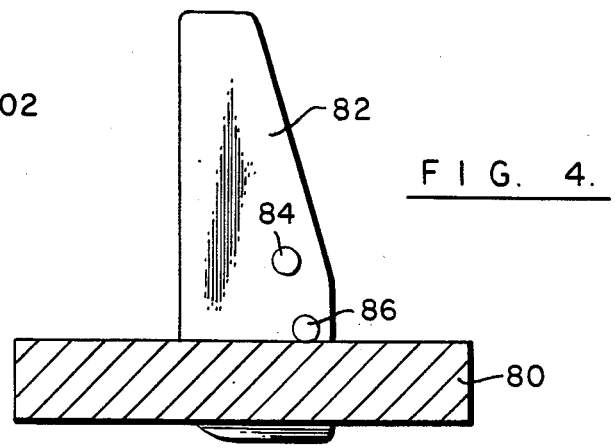
FIG. 4 if a fragmentary section showing a pivoted wire positioning block in one of its two alternative positions.
Figure 5:
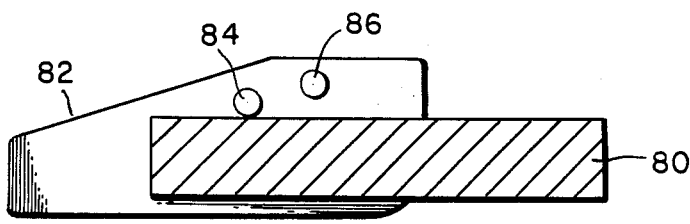
FIG. 5 is a fragmentary sectional view showing the pivoted wire positioning block in the other of its two alternative positions.

The alternative positions of the pivoted positioning block are illustrated in FIGS. 4 and 5. In FIG. 4, stop pin 86 is in engagement with plate 80, and block 82 extends upwardly to a position in which it can be engaged by the end of a straight wire blank clamped in tangent relationship to die 22. In this position, the positioning block would interfere with swinging movement of sweep arm 36. In FIG. 5, the block is pivoted downwardly to a position in which its stop pin 86 engages plate 80. In this position, clearance is provided for swinging movement of arm 36 (FIG. 1).

Figure 6:
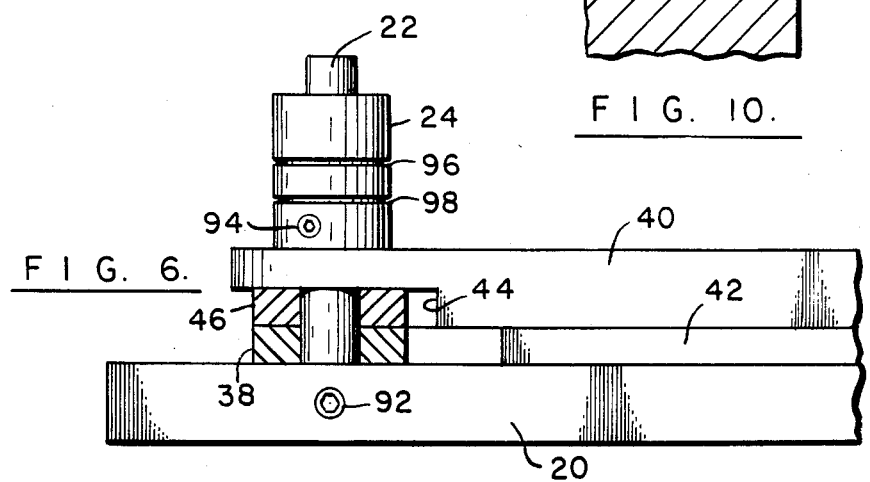
FIG. 6 is a fragmentary sectional view showing details of the die-support pin and the sweep arm pivoting means of the invention.

As shown in FIG. 6, pin 22 is secured to block 20 by a set screw 92. In a similar manner, die 24 is removably secured to pin 22 by set screw 94. Die 24 may have a single wire-receiving groove, or it may have multiple wire-receiving grooves. Die 24 has a pair of grooves 96 and 98. These grooves both lie in planes to which the axis of the die and pin 22 is perpendicular.

Figure 7:
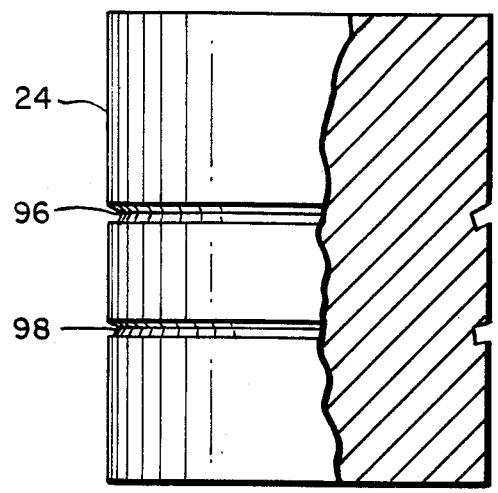
FIG. 7 is an elevational view, partly in section, showing a typical wire forming die.

The grooves of die 24 are shown in greater detail in FIG. 7. Grooves 96 and 98 are designed to receive rectangular wires and to apply torgue to the anterior segments of the arches formed from these wires. Groove 96 is cut so that it produces a torque of 20 degrees. Groove 98 produces a torque of 10 degrees. These dies can be formed with any desired number of grooves, and the number of grooves is limited only by the length of the wire-engaging rollers of the bending mechanism. Each groove on a multiple-groove die can have a torque angle different from that of each of the other grooves.

Figure 8:
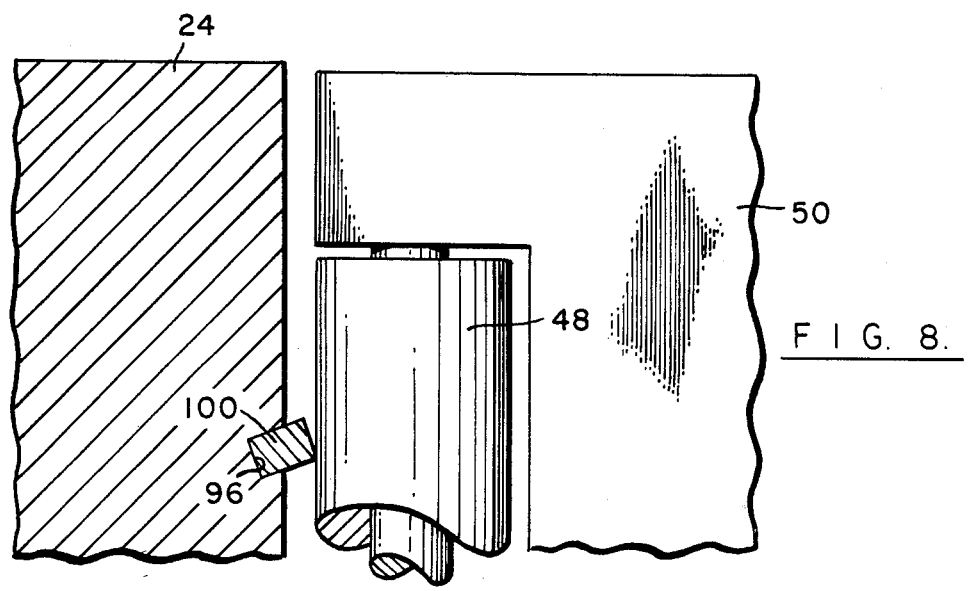
FIG. 8 is a fragmentary elevational view, partly in section, showing the die in cooperation with one of the wire-forming rollers of the bender.

In FIG. 8, roller 48 is shown in engagement with a rectangular wire 100, situated in groove 96 of die 24. Groove 96 conforms closely to three sides of wire 100. Roller 48 engages a corner of the wire, and as it moves around the die, it applies pressure to wire 100, forming the arch, and at the same time imparting a built-in torque to the anterior portion of the arch.

Figure 9:
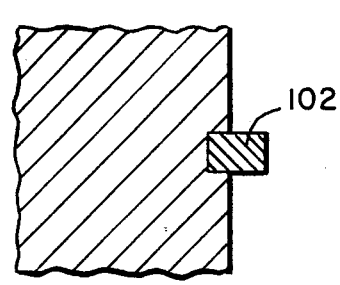
FIGS. 9–12 are fragmentary sectional views illustrating several different forms of wire-forming dies used in accordance with the invention.

The wire need not be torqued, however. In FIG. 9, a rectangular wire blank 102 is situated in a groove which has no tilt. The rollers of the bending mechanism engage the outermost face of this wire blank, and form an untorqued arch.

Figure 10:
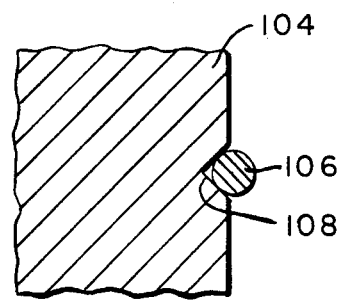

The bending apparatus of the invention is also suitable for bending wire blanks having circular cross-sections. As shown in FIG. 10, die 104 receives a circular wire blank 106 in a V-shaped groove 108. A single V-shaped groove is capable of receiving circular wires over a range of wire diameters. Adjustments of the toggle mechanisms of the sweep arms can be made to accommodate these different diameters.

Figure 11:
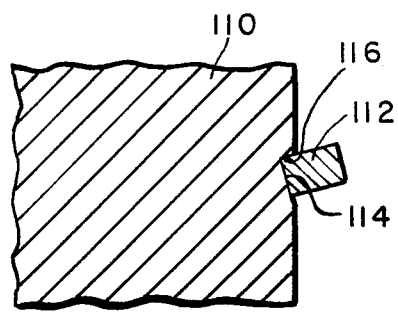

FIG. 11 shows another form of groove suitable for receiving a rectangular wire. In FIG. 11, die 110 receives wire 112 in a groove which has only two, rather than three, sides. One side, 114, extends upwardly and inwardly from the cylindrical outer face of the die, meeting overhanging groove face 116 perpendicularly. The upper left corner of the wire blank 112 conforms to the corner formed by faces 114 and 116. The roller engages the wire blank in the same manner as is depicted in FIG. 8. It is not necessary to provide a groove with a lower wire-supporting face, as the clamping mechanism will hold a wire in place in the groove of FIG. 11 just as well as it holds a wire in place in the groove of FIG. 8.

Figure 12:
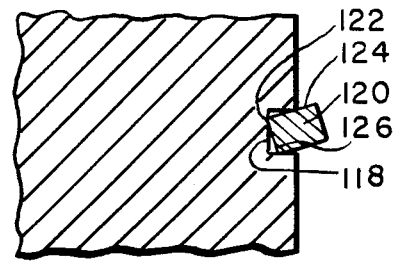
Figure 13:
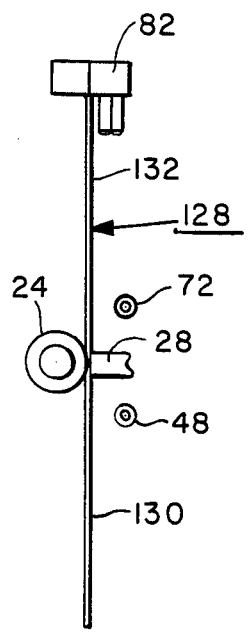
FIGS. 13–16 are schematic views of the bender showing the essential steps in the formation of an orthodontic arch wire.
Figure 14:
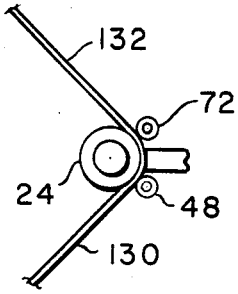

It is possible to use a groove which is slightly larger than the wire blank to produce a torqued wire. This is depicted in FIG. 12, in which a rectangular wire blank 120 is received in groove 118. The groove is rectangular in shape, and has upper and lower faces perpendicular to the cylindrical outer surface of the die. Corner 122 of the wire contacts the inner wall of the groove. Upper face 124 of the wire contacts the corner at which the upper wall of the groove meets the face of the die. Corner 126 of the wire contacts the lower face of the groove. The relationship between the thickness of the wire, and the dimensions of the groove determines the degree of torque.

The manner of forming an orthodontic arch from a straight wire blank is depicted in FIGS. 13–16, which show the essential successive steps. A wire blank 128, which is a straight length of wire seven inches in length, is clamped into a groove in die 24 by wire-engaging face part 28 of the clamping mechanism. Segment 130 extends in one direction from the point at which the wire is tangent to the die, and segment 132 extends in the other direction. Each of these segments is three and one-half inches long. Segment 132 engages the face of positioning block 82, thereby insuring that the exact center point of the wire touches the die. Rollers 48 and 72 of the sweep arms are initially spaced away from the wire as the wire is clamped into place. However, upon operation of the toggles on the sweep arms, these rollers are moved to positions closely adjacent to the point at which the wire is tangent to the die. Preferably, the rollers are positionable so that they engage the wire at positions no more than approximately 45 degrees away from the tangent point.

After the wire is clamped into place, the toggle mechanisms of the sweep arms are operated to move rollers 48 and 72 into contact with segments 130 and 132 respectively of the wire blank. This operation causes the segments to move into positions depicted in FIG. 14. The toggle mechanisms of the sweep arms are adjusted to apply the same amount of pressure to both wire segments.

Figure 15:
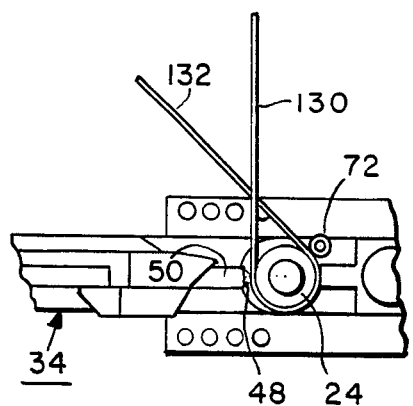

Sweep arm 34 is then moved so that its roller 48 moves around the die while constantly in contact with wire segment 130. Normally, the arm will move at least to the position, as shown in FIG. 15, in which it is directly opposite to the point at which the wire is clamped to the die by the clamping means. The arm can be moved farther than this, however, and stop pins can be placed in selected holes in block 20 to ensure consistency in the formation of successive arch wires. At all times during movement of the sweep arm, the distance between the roller and the die is constant.

Figure 16:
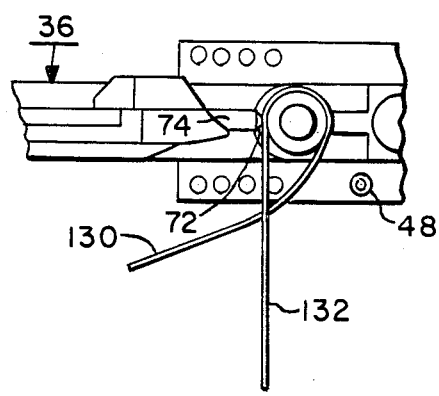

The next step is to operate the toggle mechanism of arm 34 to withdraw its slide 50, and thereby cause roller 48 to move away from wire segment 130. Arm 34 is then rotated counterclockwise to its initial position, and wire segment 130 then assumes a position and curvature substantially as shown in FIG. 16. Arm 36 is then moved about the die in a counterclockwise direction, as viewed in FIG. 16. Its roller 72 continuously presses against wire segment 132 while remaining at a constant spacing from the die. Slide 74 is then withdrawn, and arm 36 returned to its initial position as depicted in FIG. 1. Following this, the clamping mechanism is released, and the formed orthodontic arch is removed from the bending device.

The invention enables the orthodontist to make high-quality arches in his own office rapidly and inexpensively.

Numerous modifications can be made to the apparatus described without departing from the scope of the invention as defined in the following claims.

I claim:

1. A sweep-arm bender for forming orthodontic arches from straight wire blanks comprising:

a die having a cylindrical surface and a wire-receiving groove in said surface, the groove being situated in a plane perpendicular to a die axis about which the cylindrical surface is symmetrical;

clamping means, connected to the die and movable toward and away from said cylindrical surface, for temporarily engaging a wire blank and applying a clamping force to the wire blank, thereby firmly holding a portion of the wire blank in the groove of the die;

first and second sweep arms, each pivoted on said die axis;

a slide on each of said sweep arms, and guide means on each of said arms constraining its slide to movement toward and away from said die axis;

bearing means on each slide and a circular cylindrical roller carried by each slide, each roller being mounted in the bearing means on its slide for rotation about a roller axis which is parallel to the die axis, and each roller being positioned so that it is intersected by said plane in which the wire-receiving groove is situated; and means on each arm for temporarily locking its roller in a position such that the outer roller surface is capable of pressing the wire blank into the wire-receiving groove as the arm sweeps about the die axis;

each of the arms being pivotable from a position in which its roller is located adjacent to the clamping means to a position beyond the position in which its roller is directly opposite the clamping means.

2. A bender according to claim 1 comprising a positioning block having a face, and means connected to the die for mounting the block for movement from a first position, in which it would interfere with sweeping movement of at least one of the arms and in which the face is positioned at a location such that it can be engaged by an end of a wire blank tangent to the die and extending through the wire-receiving groove, to a second position in which the block permits clear sweeping movement of the sweep arms, the means for mounting the block also insuring that the face of the block is always at a predetermined distance from the point at which the wire blank is tangent to the die when the block is in its first position.

3. A bender according to claim 2 in which the means for mounting the block is a pivoting means, and in which the face of the block is situated in a plane to which the axis of the pivoting means is perpendicular.

4. A bender according to claim 1 in which the means on each arm for temporarily locking the roller includes an operating lever movable from an unlocked position to a locking position, toggle means linking the operating lever to the slide on the arm, and means, connected to the toggle means and to the slide, for adjusting the relationship between the toggle means and the slide whereby the pressure applied by the roller to the wire blank when the lever is in its locking position can be adjusted.

5. A bender according to claim 4 in which the adjusting means allows continuous adjustment of the relationship between the toggle means and the slide, whereby the pressure applied by the roller can be adjusted continuously.

6. A bender according to claim 1 in which the wire-receiving groove in the die is shaped to conform to the cross-section of a rectangular wire blank and to position the wire blank, when held in the groove by the clamping means, so that its surfaces are oblique with respect to the die axis while the intersections of the wire surfaces are parallel to the groove.

7. A bender according to claim 1 in which the locking means on each arm allows the outer roller surface to press the wire blank into the wire-receiving groove when the roller is located adjacent to the clamping means.

8. A bender according to claim 7 in which, the locking means on each arm is movable from an unlocked condition to a locked condition, and in which the roller on each arm remains at a fixed distance from the die axis throughout the pivoting movement of the arm so long as its locking means is in the locked condition.

9. A sweep-arm bender for forming orthodontic arches from straight wire blanks comprising:
 - a die having a cylindrical surface and a wire-receiving groove in said surface, the groove being situated in a plane perpendicular to a die axis about which the cylindrical surface is symmetrical;
 - clamping means, connected to the die and movable toward and away from said cylindrical surface, for temporarily engaging a wire blank and applying a clamping force to the wire blank, thereby firmly holding a portion of the wire blank in the groove of the die;
 - at least one sweep arm pivoted on said die axis; and
 - a positioning block having a face, and means, connected to the die, for mounting the block for movement from a first position, in which it would interfere with sweeping movement of the arm and in which the face is positioned at a location such that it can be engaged by an end of a wire blank tangent to the die and extending through the wire-receiving groove, to a second position in which the block permits clear sweeping movement of the sweep arm, the means for mounting the block also insuring that the face of the block is always at a predetermined distance from the point at which the wire blank is tangent to the die when the block is in its first position.

10. A bender according to claim 9 in which the means for mounting the block is a pivoting means, and in which the face of the block is situated in a plane to which the axis of the pivoting means is perpendicular.

* * * * *